US011185733B2

(12) United States Patent
Naves

(10) Patent No.: US 11,185,733 B2
(45) Date of Patent: Nov. 30, 2021

(54) EXERCISE DEVICE

(71) Applicant: Heartly Strong LLC, Dublin, OH (US)

(72) Inventor: Sabrina Naves, Dublin, OH (US)

(73) Assignee: Heartly Strong LLC, Dublin, OH (US)

(*) Notice: Subject to any disclaimer, the term of this patent is extended or adjusted under 35 U.S.C. 154(b) by 171 days.

(21) Appl. No.: 16/593,315

(22) Filed: Oct. 4, 2019

(65) Prior Publication Data
US 2021/0101046 A1 Apr. 8, 2021

(51) Int. Cl.
A63B 21/00 (2006.01)
A47G 27/02 (2006.01)
A61F 7/02 (2006.01)

(52) U.S. Cl.
CPC ...... A63B 21/4037 (2015.10); A47G 27/0237 (2013.01); A61F 7/02 (2013.01); A61F 2007/0207 (2013.01); A61F 2007/0242 (2013.01); A61F 2007/0279 (2013.01)

(58) Field of Classification Search
CPC .... A47G 27/0237; A47G 9/10; A47G 9/1036; A47G 9/1063; A61F 7/02; A61F 2007/0207; A61F 2007/022; A61F 2007/0223; A61F 2007/0242; A61F 2007/0279; A61F 2007/108; A63B 21/4037
See application file for complete search history.

(56) References Cited

U.S. PATENT DOCUMENTS

| | | | | |
|---|---|---|---|---|
| 1,981,379 A * | 11/1934 | Thomson | ............... | A63B 23/10 606/237 |
| 4,777,855 A * | 10/1988 | Cohen | ...................... | A47G 9/10 5/636 |
| 5,402,545 A * | 4/1995 | Jolley | .................. | A61G 5/1043 5/653 |
| 5,689,844 A * | 11/1997 | Liu | .......................... | A47G 9/10 5/636 |
| 5,918,333 A * | 7/1999 | Takashima | ............. | A47G 9/007 5/641 |
| 6,305,040 B1 * | 10/2001 | Myler | .................... | A61H 39/04 5/630 |
| 6,766,536 B1 * | 7/2004 | Aarons | ................ | A41B 11/008 2/161.3 |
| 7,383,591 B1 * | 6/2008 | Getzwiller | ............. | A63B 71/14 2/161.1 |

(Continued)

Primary Examiner — David R Hare
(74) Attorney, Agent, or Firm — Frost Brown Todd LLC

(57) ABSTRACT

An exercise device is provided with a first element disposed at a first side and a second element disposed at a second side. The first element includes gripping features to prevent skidding or sliding of exercise device when first element is abutting a surface. The second element includes sliding features to facilitate sliding of exercise device when second element is abutting the surface. Thus, when an exercise practitioner desires to use the exercise device to prevent movement of a particular body part against the surface, the practitioner places the first element against the surface. Conversely, when the exercise practitioner desires to use the exercise device to facilitate movement of a particular body part against the surface, the practitioner places the second element against the surface. The exercise device further includes an insert which may be removed and heated or cooled to provide heating or cooling pad/pack to a body part.

12 Claims, 9 Drawing Sheets

(56) References Cited

U.S. PATENT DOCUMENTS

| | | | | |
|---|---|---|---|---|
| 7,530,127 | B2* | 5/2009 | Leifermann | A47G 9/1081 |
| | | | | 5/490 |
| 8,220,087 | B2* | 7/2012 | Villa | A63B 21/4037 |
| | | | | 5/420 |
| 8,382,645 | B2* | 2/2013 | Mylrea | A63B 21/4035 |
| | | | | 482/51 |
| 8,516,638 | B2* | 8/2013 | Kummerfeld | A47D 13/083 |
| | | | | 5/636 |
| 8,677,532 | B2* | 3/2014 | Legare | A47G 27/0237 |
| | | | | 5/652 |
| 8,931,127 | B1* | 1/2015 | Moses | A47C 27/15 |
| | | | | 5/652 |
| 9,555,275 | B1* | 1/2017 | Izzolo, Jr. | B32B 5/18 |
| 9,756,968 | B1* | 9/2017 | Gewant | A47G 9/1081 |
| 10,512,814 | B1* | 12/2019 | Conroy | A63B 22/20 |
| 2004/0250346 | A1* | 12/2004 | Vasishth | A47G 27/0237 |
| | | | | 5/417 |
| 2005/0091725 | A1* | 5/2005 | Alley | A41B 11/008 |
| | | | | 2/139 |
| 2007/0275827 | A1* | 11/2007 | Glaser | A63B 21/4037 |
| | | | | 482/23 |
| 2008/0092269 | A1* | 4/2008 | Schox | A61F 5/0118 |
| | | | | 2/159 |
| 2009/0276957 | A1* | 11/2009 | Boitet-Ball | A47G 27/0237 |
| | | | | 5/420 |
| 2012/0076981 | A1* | 3/2012 | Franks | A63B 21/4037 |
| | | | | 428/138 |
| 2013/0252791 | A1* | 9/2013 | Chang | A63B 23/1209 |
| | | | | 482/132 |
| 2013/0263377 | A1* | 10/2013 | Wootten, Jr. | A47C 27/15 |
| | | | | 5/640 |
| 2016/0287472 | A1* | 10/2016 | Starzhynskaya | A61H 39/04 |
| 2017/0072259 | A1* | 3/2017 | Trenkle | A63B 21/4034 |

* cited by examiner

EXERCISE DEVICE

BACKGROUND

In some instances, it may be desirable for exercise practitioners to perform exercises where both static and dynamic poses are performed in the same exercise session for improving strength, flexibility, and balance. Hereinafter "yoga" will be used to describe such exercise.

Yoga is a group of spiritual, physical, and mental practices or disciplines which originated in ancient India. Yoga consists largely of postures called "asanas." Asana was originally referred to as a sitting pose for meditation. Modern yoga has developed beyond a form of meditation into a form of exercise. In modern yoga, many anasas have been added incorporating reclining, standing, inverting, twisting, and balancing. Asanas are also called "yoga poses." Generally, yoga poses are static poses. Static poses are poses that the practitioner holds for an extended period without moving along a supporting structure such as a floor. Some examples of static poses include: headstand, camel, puppy pose, cobra, baby cobra, low lunge, high plank, table top, chin stand, sitting lotus, forearm side plank, corpse pose, child's pose, twisted low lunge, balancing table top, rabbit, gate pose, and tiger pose.

In addition to static poses, the exercise practitioner may also practice dynamic poses. Dynamic poses allow for movement of the practitioner's body along the floor. This movement is typically some form of sliding into a stretching position. Some examples of dynamic poses include splits, cat/cow, frog pose, high plank, half straddle, straddle, utthita namaskarasana and chaturanga. Dynamic poses often use movement of a body part along the floor which may be uncomfortable for the practitioner if performed on a hard floor. Other examples of dynamic poses are vinyasas. Vinyasas are movements between poses in yoga, typically accompanied with coordinated breathing such as chaturanga.

Traditionally, a yoga mat is used to support and comfort the practitioners. If the practitioner desires additional comfort on a knee or elbow beyond that offered by the yoga mat, a common practice is to fold the yoga mat upon itself or use a towel to provide additional comfort.

Yoga mats are generally rectangular in shape and have a narrow side that is approximately two feet wide and a long side that is approximately six feet wide. Yoga mats can be cumbersome to transport to and from yoga class. A full classroom using yoga mats can limit the number of practitioners that a classroom will hold. Often, practitioners perform exercise on the yoga mat facing the narrow side. A knee or an elbow can extend beyond the width of the narrow side of the yoga mat engaging the floor which causes the practitioner discomfort.

Yoga mats provide an increased friction between the body and floor or "tack" to aid the practitioner so that hands, feet, and joints do not slip or slide on the floor when performing static poses. Yoga mats are generally made from vinyl or PVC. Many exercise practitioners are now seeking environmentally friendly materials to complement their practice. Eco-friendly mats tend not to be treated with the same chemicals and offer little or no tack. Practitioners, depending on their practice, may purposely chose a mat having a desired amount of tack. However, when performing dynamic poses, the yoga mat may bind upon the body not allowing the body to slide. The practitioner may remedy this situation by doing the dynamic pose on the floor without the comfort of the yoga mat.

Additionally, yoga practice often incorporates restorative poses. Restorative poses are poses that allows complete relaxation and rest for the body. A common restorative pose is savasana, or corpse pose. Heat or cold can be applied to the body during restorative poses to further relax and soothe the body. Generally, this heat or cold has been applied with an ice pack or a heating pad.

There is a need for a compact exercise device that allows a hand, foot, knee, or elbow to slide upon the floor in some instances, and in other instances the exercise device inhibits sliding of the hand, foot, knee, elbow, or head. In other instances, there is a need for an exercise device that retains heat or cold and be applied to the body to aid relaxation and soothe the body.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
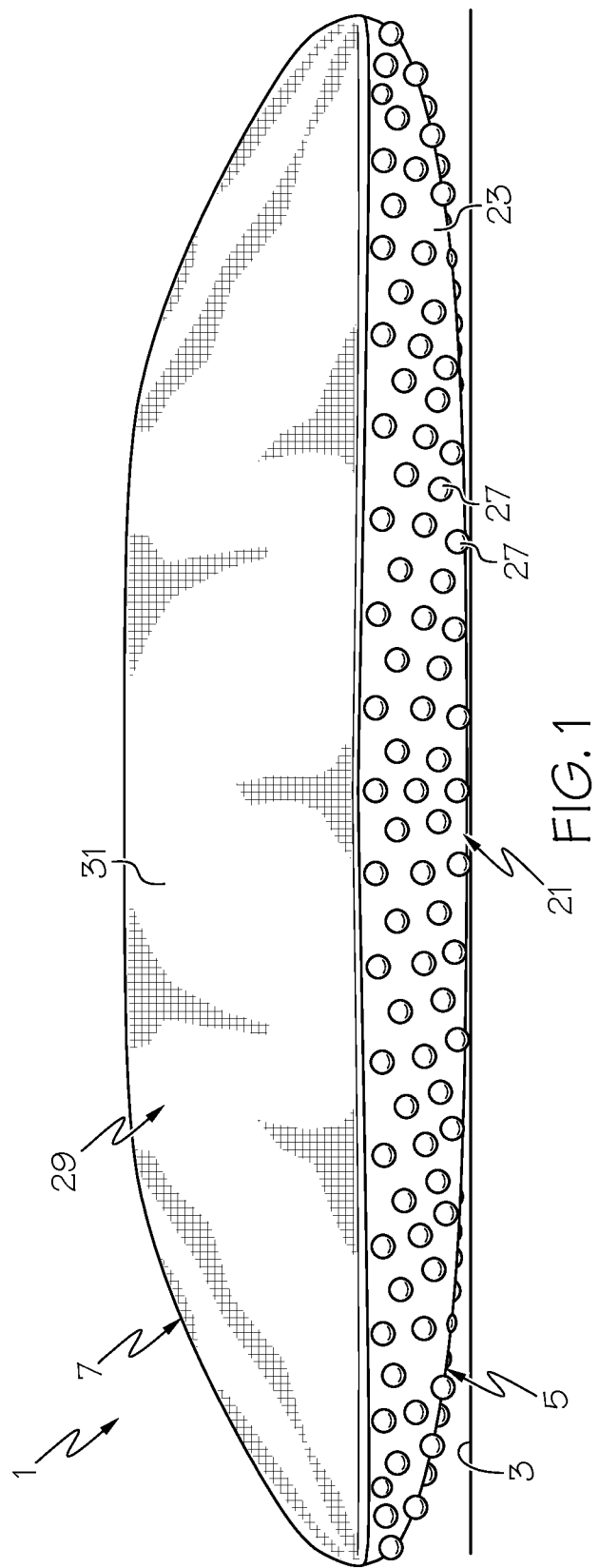
FIG. 1 depicts a side perspective view of an exemplary exercise device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It will be appreciated that the terms "top" and "bottom" are used herein with reference to an exercise device in relation to a supporting structure. "Top" and "bottom" references the orientation of the exercise device in relation to the supporting structure. "Bottom" is located proximate in relation to the supporting structure and "top" is located distal in relation to the supporting structure. For example, the planar side that contacts the supporting structure is on the bottom, and the planar side that does not contact the supporting structure is on the top. It will be further appreciated that, for convenience and clarity, spatial terms such as "left," "right," "side," "axial," and "longitudinal" also are used herein for reference to relative positions and directions.

I. CONSTRUCTION OF EXERCISE DEVICE

Figure 2:
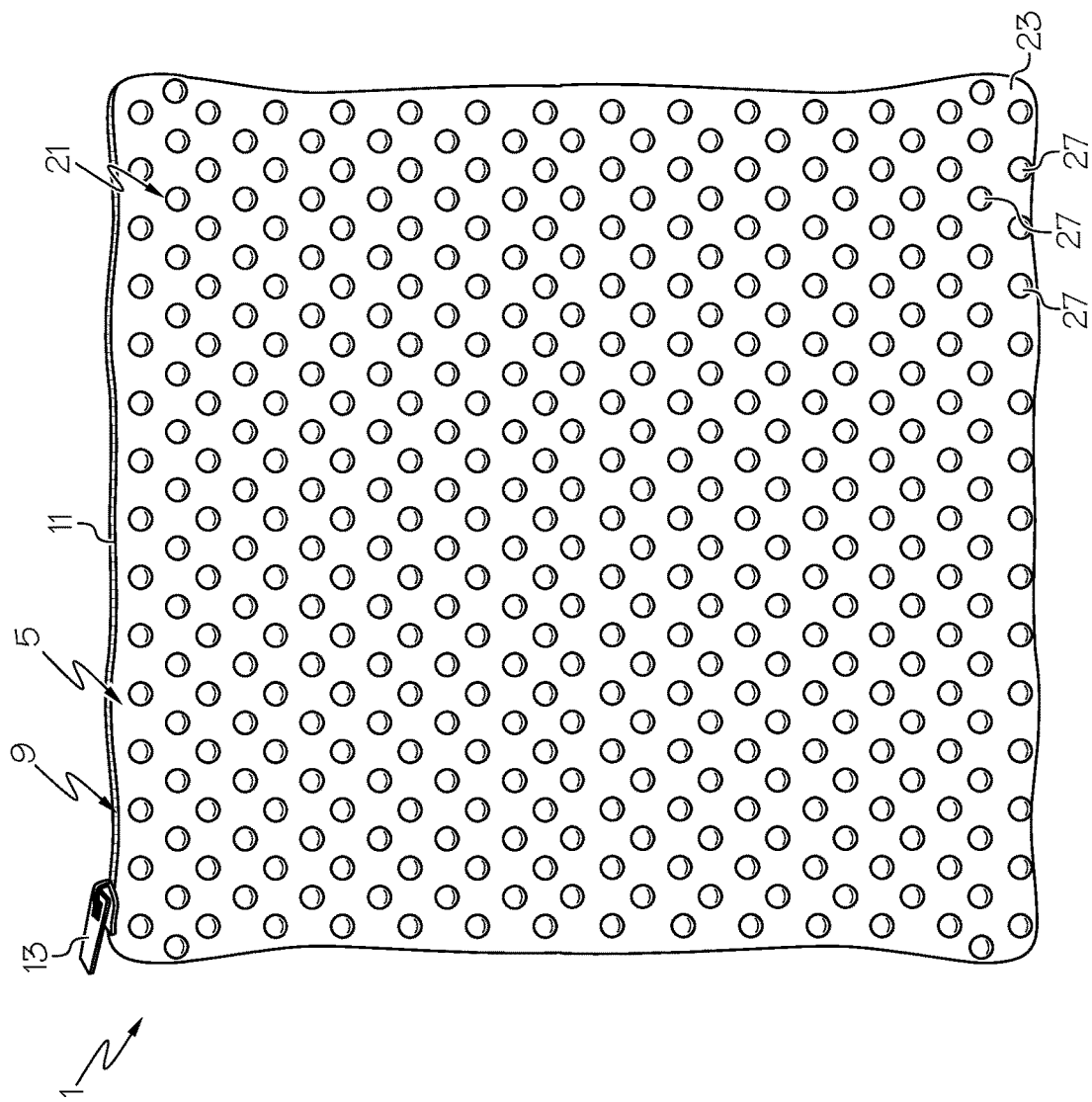
FIG. 2 depicts a top view of a first side of the exercise device of FIG. 1 showing an exemplary gripping element.
Figure 3:
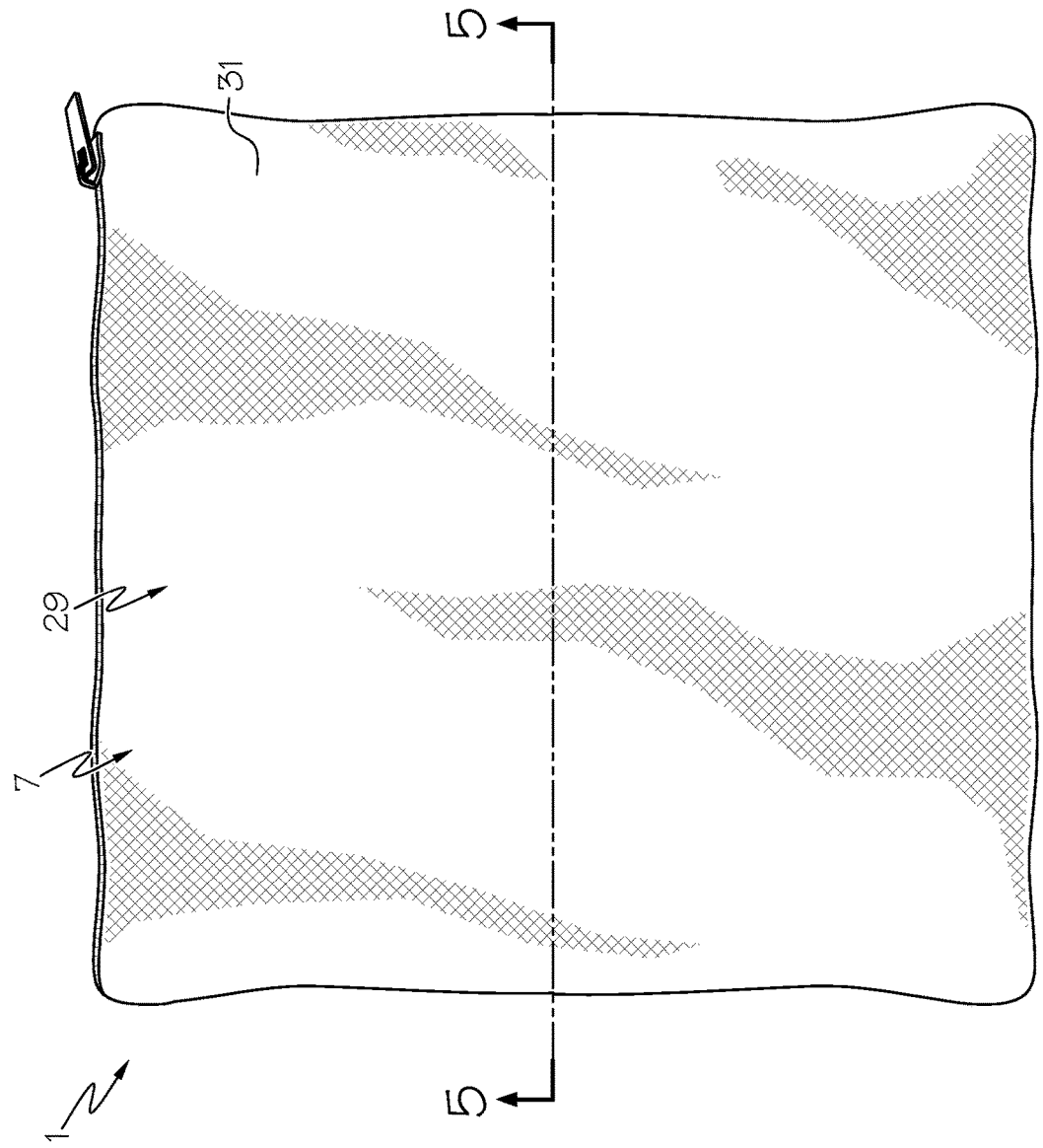
FIG. 3 depicts a top view of a second side the exercise device of FIG. 1 showing an exemplary sliding element.

FIG. 1-3 shows an exemplary exercise device (1) on a supporting structure such as a surface (3), which may be comprised of a floor of an exercise studio or home. These floors are often constructed of hardwoods, synthetic wood, or concrete. Alternatively, surface (3) may be a yoga mat, padding, or any other structure disposed between the actual floor and exercise device (1). Inasmuch as exercise device (1) is generally sized to be transported easily by a user, the particular surface (3) interacting with exercise device (1) may change frequently, as the user may take exercise device (1) to different locations or environments. In some versions of exercise device (1), the length and width are generally similar sizes. In some versions, the length and width are both between five and seven inches.

Exercise device (1) includes a first side (5) and a second side (7). In general, first side (5) includes features for preventing or reducing sliding of exercise device (1) on surface (3), while second side (7) includes features for facilitating sliding of exercise device (1) on surface (3). The user may face first side (5) down to abut surface (3) when doing static exercises requiring stationary poses and minimal sliding of exercise device (1). Conversely, the user may face second side (7) down to abut surface (3) when doing dynamic exercises requiring movement to facilitate sliding of exercise device (1).

Figure 4:
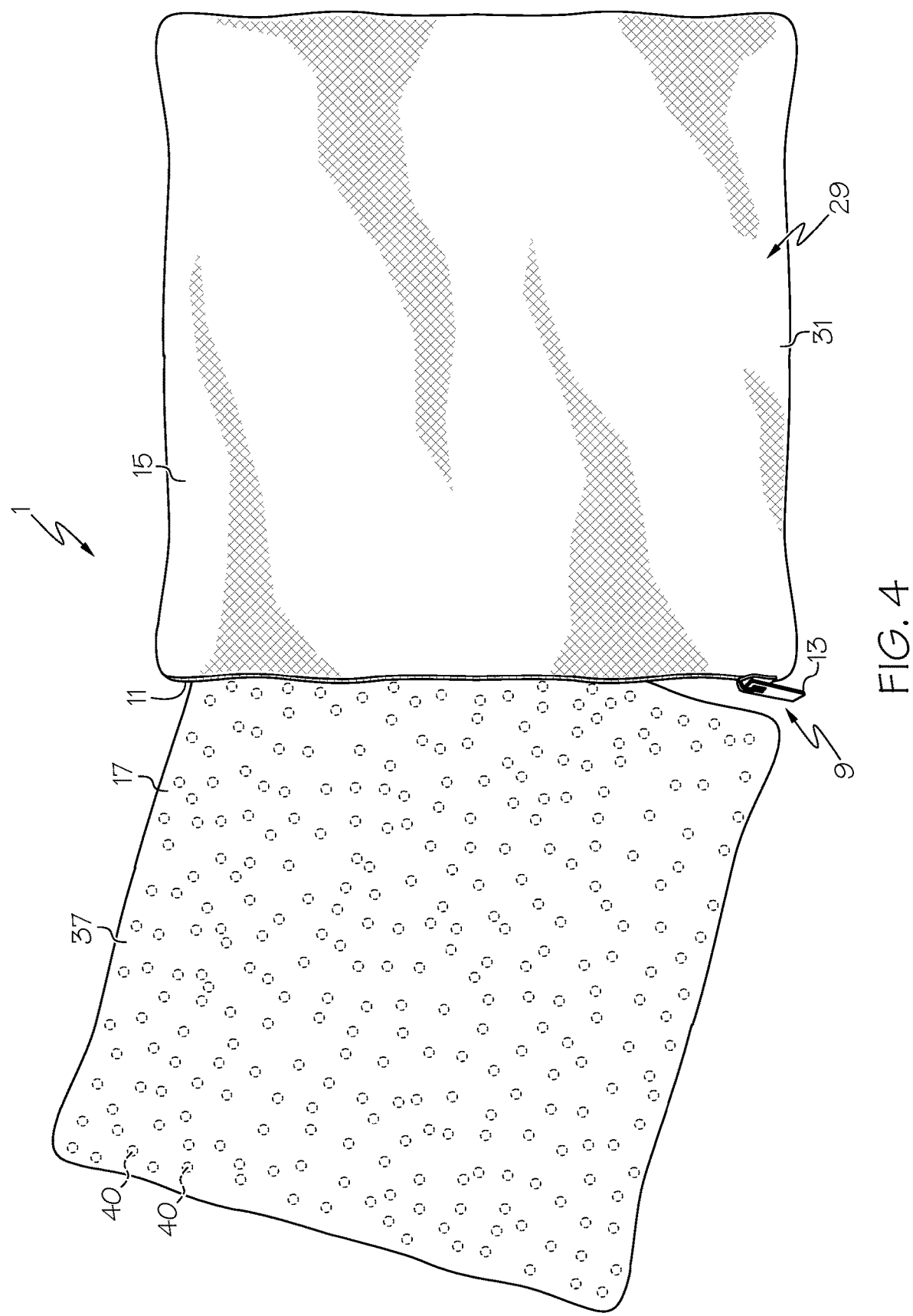
FIG. 4 depicts a top view of an exemplary insert and exemplary holder of the exercise device of FIG. 1.

A zipper assembly (9) is disposed at an end of exercise device (1), between first side (5) and second side (7). Zipper assembly (9) comprises a plurality of teeth (11) and a zipper (13) for transitioning zipper assembly (9) between a closed orientation (FIG. 2) and an open orientation (FIG. 4).

As shown in FIGS. 1-4, in general, exercise device (1) is comprised of a pouch (15), which acts as the outer sleeve or bag for holding an insert (17) therein. Pouch (15) may be machine washable for removing sweat and other debris or bacteria. Pouch (15) defines a pocket (19) therein and insert (17) is sized to be selectively disposed within pocket (19). Zipper assembly (13) is used to open and close pocket (19).

As zipper assembly (9) moves from the open orientation (FIG. 4) to the closed orientation (FIG. 2), pocket (19) is closed. Conversely, as zipper assembly (9) moves from the closed orientation (FIG. 2) to the open orientation (FIG. 4), pocket (19) is opened and exposed to the user.

Figure 5:
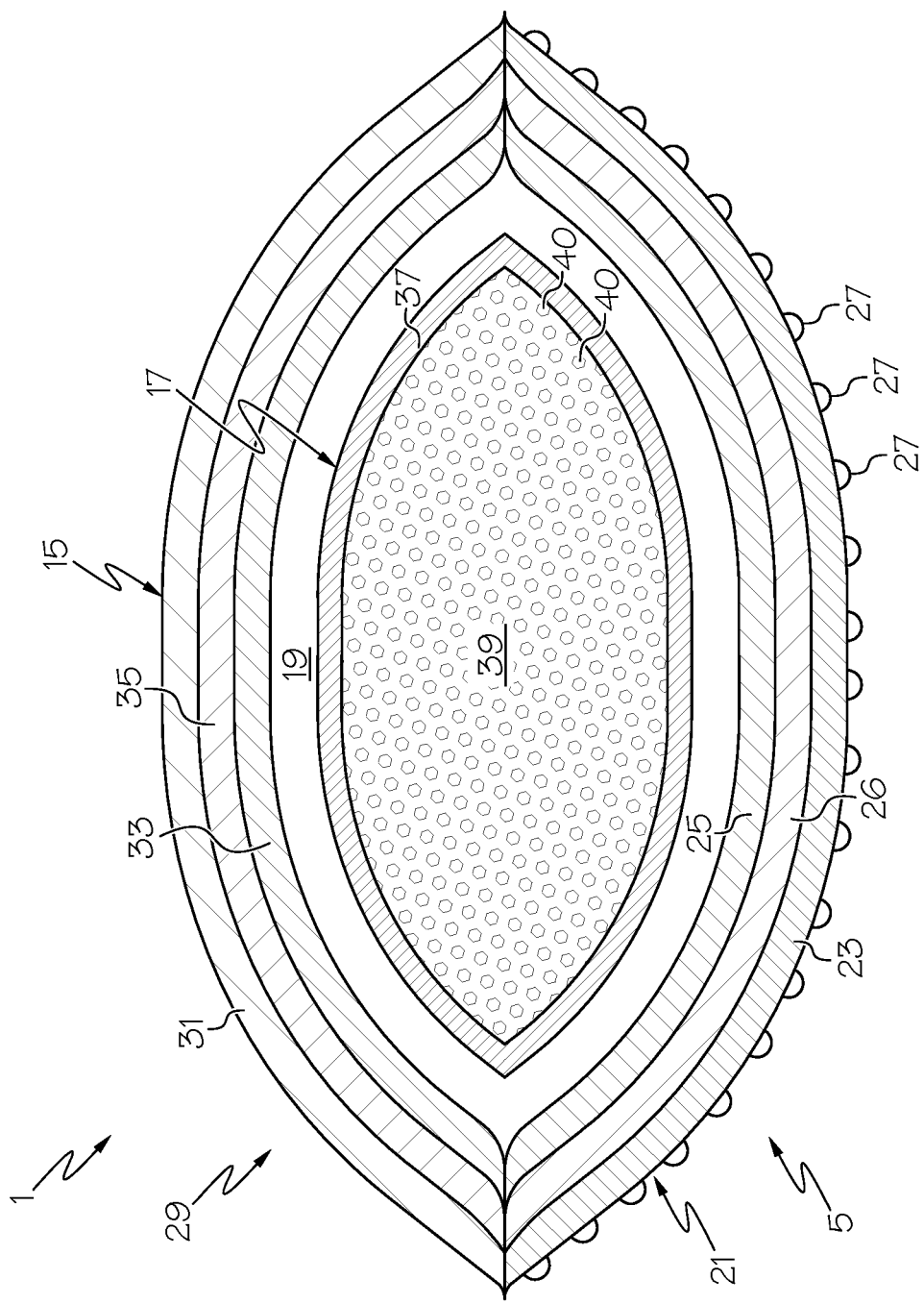
FIG. 5 depicts a cross-sectional of the exemplary exercise device of FIG. 1 taken along section line 5-5 of FIG. 3.

Pouch (15) of exercise device (1) comprises a gripping element, referred to hereinafter as a first element (21). First element (31) is disposed at first side (5) of exercise device (1). First element (21) comprises a first outer layer (23) and a first inner layer (25). First outer layer (23) may comprise a gripping fabric. A "gripping fabric" is typically a cotton-based fabric with gripping features applied thereto such a elastomeric or plastic sections to increase friction and reduce slipping or sliding when abutted against a surface. A griping fabric may also include a plurality of nodules or nubs to facilitation the "gripping" of first element (21) to surface (3). To illustrate, as shown in FIGS. 1, 2, and 5, a plurality of gripping nodules (27) may be disposed on first outer layer (23). Each nodule (27) may be comprised of an elastomeric, plastic, rubber, non-slip, non-skid, or other similar material. When used in this context, the terms "grip," "gripping," "non-slip," and/or "non-skid" are used to signify properties that increase the frictional coefficient associated with first element (21) and surface (3) when first element (21) is engaged with surface (3) and a force is applied thereto.

As shown in FIG. 5, a first intermediate layer (26) may be disposed between first outer layer (23) and first inner layer (25). First intermediate layer (26) may be comprised of an antimicrobial material constructed to inhibit the growth of microbials such as bacterial. The antimicrobial effect may be via an antimicrobial layer applied to the material comprising first intermediate layer (26). First intermediate layer (26) may be comprised of batting material, such as cotton, polyester, wool, or bamboo batting.

Pouch (15) of exercise device (1) comprises a sliding element, referred to hereinafter as a second element (29). Second element (29) is disposed at second side (7) of exercise device (1). Second element (29) comprises a second outer layer (31) and a second inner layer (33). Some versions of second outer layer (31) may comprise a wicking performance fabric and/or a synthetic fabric such as nylon, polyester, polyvinyl chloride, or rayon. The term "synthetic fabric" refers to the class of fabrics which are artificial or man-made, not generally found in nature, and are created using chemical synthesis or similar techniques. More specifically, many synthetic fabrics are made by joining monomers into polymers, by the process of polymerization. This class of fabric are generally more "slippery" or prone to sliding over surfaces more easily than non-synthetic fabrics.

Second outer layer (31) may comprise a smooth, easily slidable surface with properties that decrease the frictional coefficient associated with second element (29) and surface (3) when second element (29) is engaged with surface (3) and a force is applied thereto. Second outer layer (31) may include a coating or other features to increase the sliding or slipping ability of second element (29) when second element (29) abuts surface (3) or to add or increase the antimicrobial properties of second outer layer (31).

As shown in FIG. 5, similar to first intermediate layer (26), a second intermediate layer (35) may be disposed between second outer layer (31) and second inner layer (33). Second intermediate layer (35) may be comprised of an antimicrobial material constructed to inhibit the growth of microbials such as bacterial. The antimicrobial effect may be via an antimicrobial layer applied to the material comprising second intermediate layer (35). Second intermediate layer

(35) may be comprised of batting material, such as cotton, polyester, wool, or bamboo batting.

First outer layer (23) and second outer layer (31) are different. More specifically, the materials and/or properties associated with first outer layer (23) are different from the materials and/or properties associated with second outer layer (31). In furtherance of the gripping features of first outer layer (23), first outer layer (23) is associated with a first frictional coefficient when moved along surface (3). In furtherance of the slipping features of second outer layer (31), second outer layer (31) is associated with a second frictional coefficient when moved along surface (3), wherein the first frictional coefficient is greater than the second frictional coefficient.

Thus, a user desiring to exploit the materials and/or properties associated with first outer layer (23) orients first outer layer (23) to abut against surface (3) as the user is using exercise device (1). Inasmuch as the material and/or properties of first outer layer (23) are directed to non-skid and non-slip features, when a force is applied by the user to exercise device (1), the material and/or properties associated with first outer layer (23) act to prevent the sliding or slipping of exercise device (1) against surface (3).

Conversely, a user desiring to exploit the materials and/or properties associated with second outer layer (31) orients second outer layer (31) to abut against surface (3) as the user is using exercise device (1). Inasmuch as the material and/or properties of second outer layer (31) are directed to slipping and sliding features, when a force is applied by the user to exercise device (1), the material and/or properties associated with second outer layer (31) act to facilitate the sliding and slipping of exercise device (1) against surface (3).

While first outer layer (23) is comprised of a first fabric and second outer layer (31) is comprised of a second fabric, first inner layer (25) and second inner layer (33) may both be comprised of a third fabric. This third fabric may be any type of fabric, including cotton, polyester, and/or wool-based fabric.

As shown in FIG. 5, pocket (19) is defined by pouch (15) between first element (21) and second element (29). Pocket (19) is sized to selectively receive insert (17) therein and insert (17) is sized to be selective disposed in pocket (19). Insert (17) comprises an outer layer (37) and an internal cavity (39) defined by outer layer (37). Outer layer (37) may be a cotton muslin fabric, a 100% cotton fabric, or other similar fabric. A plurality of granules (41) such as millet are disposed in internal cavity (39). In some versions of insert (17), plurality of granules (40) weigh approximately one half of a pound total. Each granule in plurality of granules (41) may be both freezable and microwavable to capture cold or heat, respectively. Thus, a user may remove insert (17) from pocket (19) and microwave it or otherwise impart heat into insert (17) to form a heating pad for the user. Conversely, a user may freeze or otherwise impart cold into insert (17) to form an ice pack for the user.

II. METHODS OF USING EXERCISE DEVICE

Figure 6:
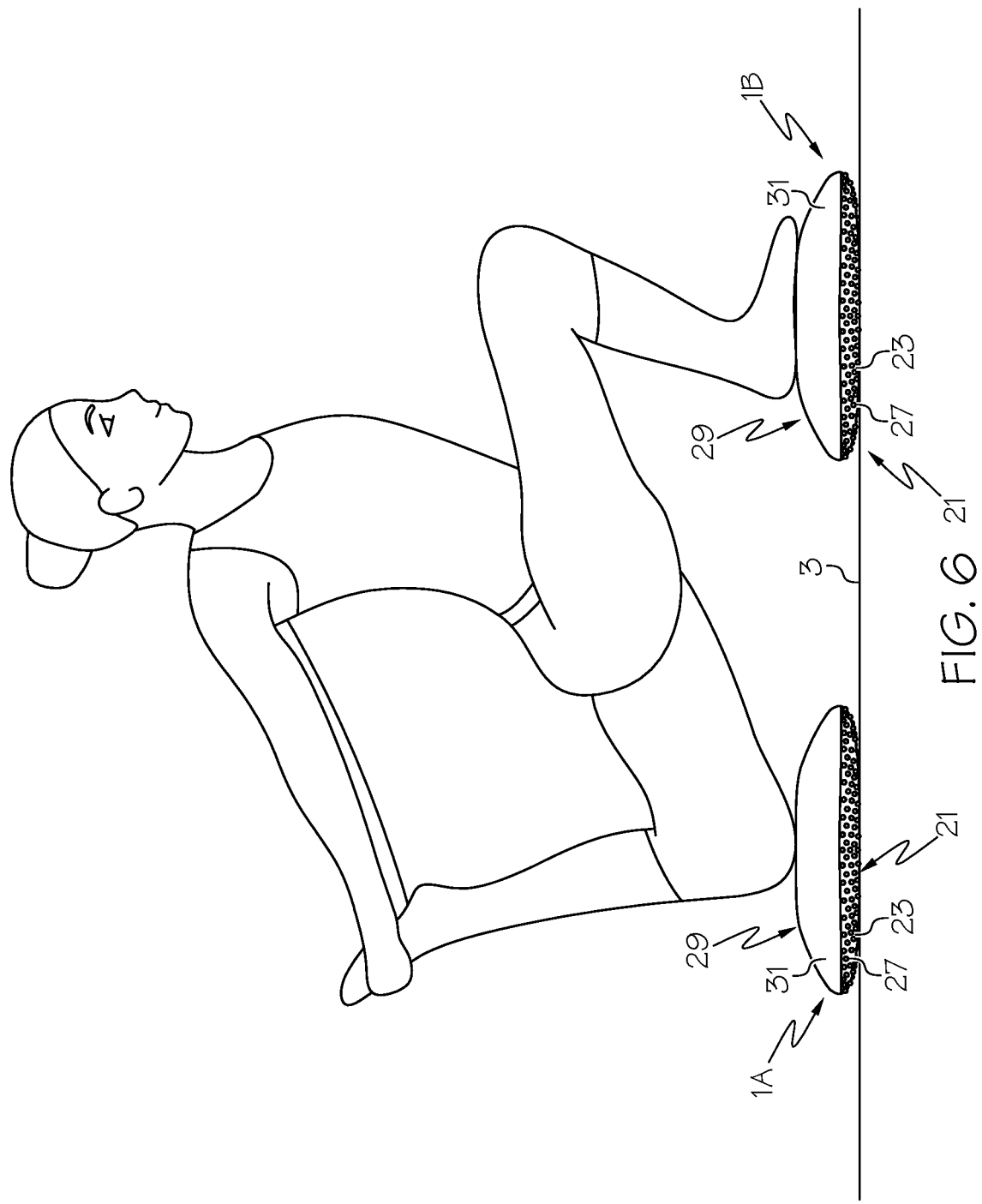
FIG. 6. depicts a perspective view of an exercise practitioner using the exercise device of FIG. 1 in an exemplary static pose.
Figure 7:
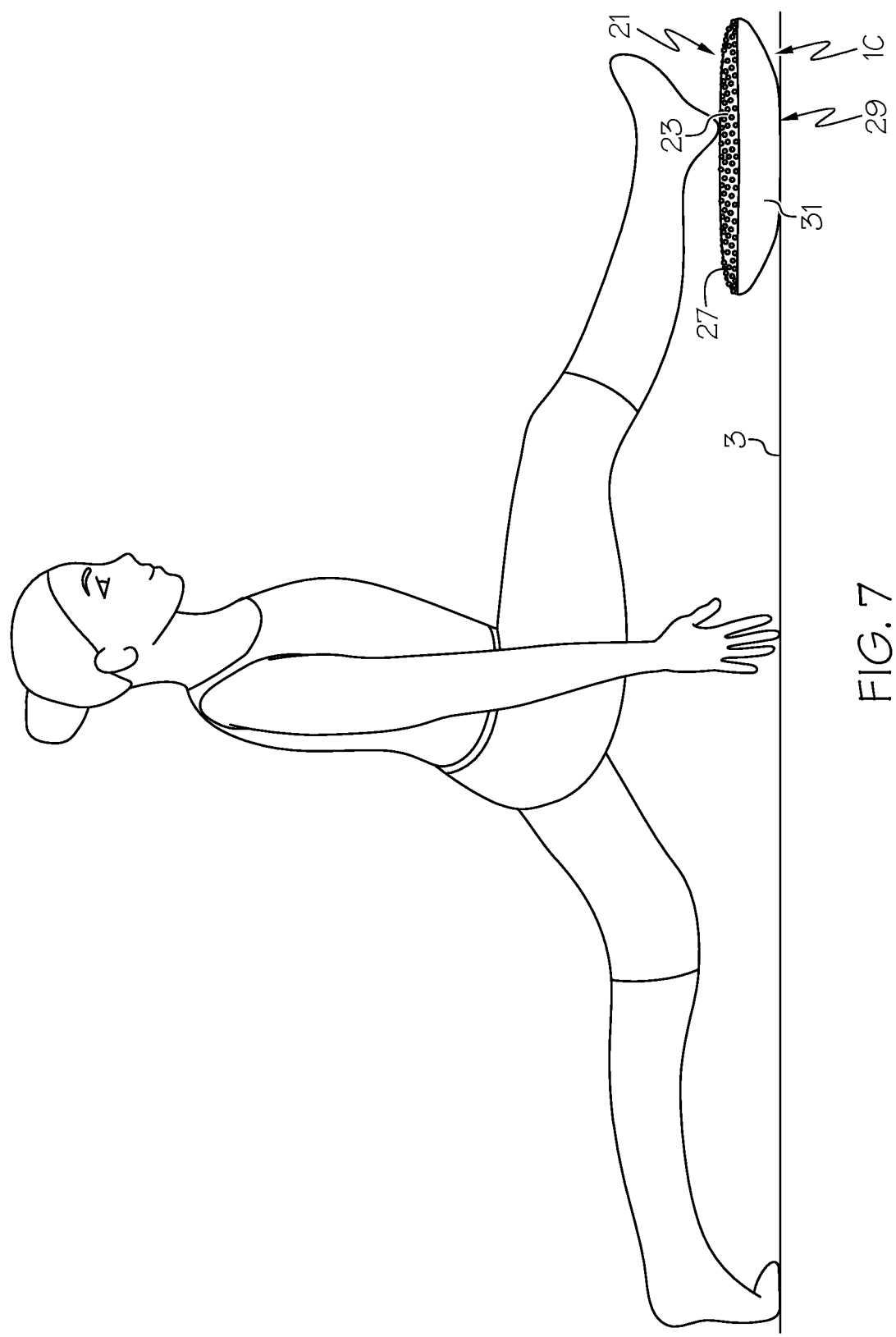
FIG. 7 depicts a perspective view of an exercise practitioner using the exercise device of FIG. 1 in an exemplary dynamic pose.

FIGS. 6 and 7 depict a user of exercise device (1) as a practitioner of yoga, or simply "practitioner." In FIG. 6, the practitioner is using exercise device (1) to assist in a static pose, while in FIG. 7, the practitioner is using exercise device (1) to assist in a dynamic pose. More specifically, in FIG. 6, an exercise device (1A) is placed between the practitioner's knee and surface (3), while an exercise device (1B) is placed between the practitioner's foot and surface (3). Both exercise devices (1A, 1B) are in a first orientation with respect to surface (3) with the gripping first element (21) of each exercise device (1A, 1B) abutting surface (3). Inasmuch as first outer layer (23) of first element (21) is comprised of a non-skid or non-slip fabric, as the practitioner pushes against exercise device (1A, 1B) during the static pose, neither exercise device (1A, 1B) moves or slides in response to this force. Thus, rather than the knee and foot of the practitioner bracing directly against surface (3), which may be hard and generally less pleasing than a softer material, the practitioner may dispose exercise device (1A, 1B) between the practitioner's knee/foot and surface (3) to provide cushioning without introducing sliding or slipping into the static pose.

In FIG. 7, the practitioner is using exercise device (1) to assist a dynamic pose, depicted as a "split." More specifically, in FIG. 7, an exercise device (1C) is placed between the practitioner's front foot and surface (3). Inasmuch as the practitioner is performing a dynamic pose, exercise device (1C) is in a second orientation with respect to surface (3), with the sliding second element (29) abutting surface (3). This allows the practitioner to slide the practitioner's front foot out into the stretch, as second outer layer (31) is directed to facilitating sliding movement of the practitioner. Without exercise device (1C), it would be more difficult for practitioner to slide the practitioner's front foot because of its abutment with surface (3).

The first orientation and the second orientation of exercise device (1) allows the practitioner to decide whether the practitioner intends to "grip" or "slide" a body part against surface (3). Thus, there exists a particular "sliding force" whereby in the first orientation, first outer layer (23) prevents pouch (15) from sliding on surface (3) in response to the sliding force. In the second orientation, second outer layer (31) allows pouch (15) to slide on surface (3) in response to the sliding force.

Figure 8:
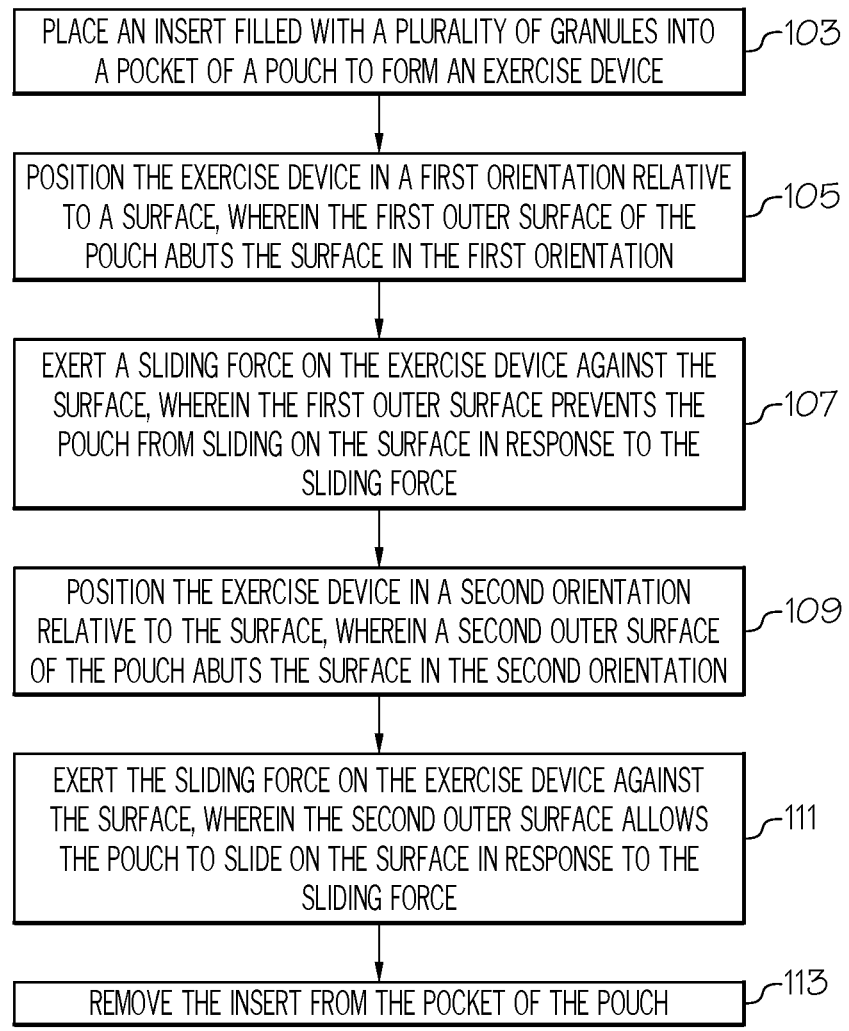
FIG. 8 depicts a diagrammatic view depicting a method of using exercise device of FIG. 1.

As shown in FIG. 8, a method (101) is provided to illustrate the above features of exercise device (1). Method (101) begins with a step (103), whereby insert (17) filled with plurality of granules (27) is disposed into pocket (19) of pouch (15) to form exercise device (1). Thereafter step (103) proceeds to a step (105). In step (105), exercise device (1) is positioned in a first orientation relative to surface (3), wherein first outer layer (23) of pouch (15) abuts surface (3) in the first orientation. Thereafter step (105) proceeds to a step (107). In step (107), a sliding force is exerted on exercise device (1) against surface (3), wherein first outer layer (23) prevents pouch (15) from sliding on surface (3) in response to the sliding force. Thereafter step (107) proceeds to a step (109). In step (109), exercise device (1) is positioned in the second orientation relative to surface (3), wherein second outer layer (31) of pouch (15) abuts surface (3) in the second orientation. Thereafter step (109) proceeds to a step (111). In step (111), the sliding force is exerted on exercise device (1) against surface (3), wherein second outer layer (31) allows pouch (15) to slide on surface (3) in response to the sliding force. Thereafter step (111) proceeds to a step (113). In step (113), insert (17) is removed from pocket (19) of pouch (15). Thereafter, method (101) proceeds to end.

III. HEATING AND COOLING

Figure 9:
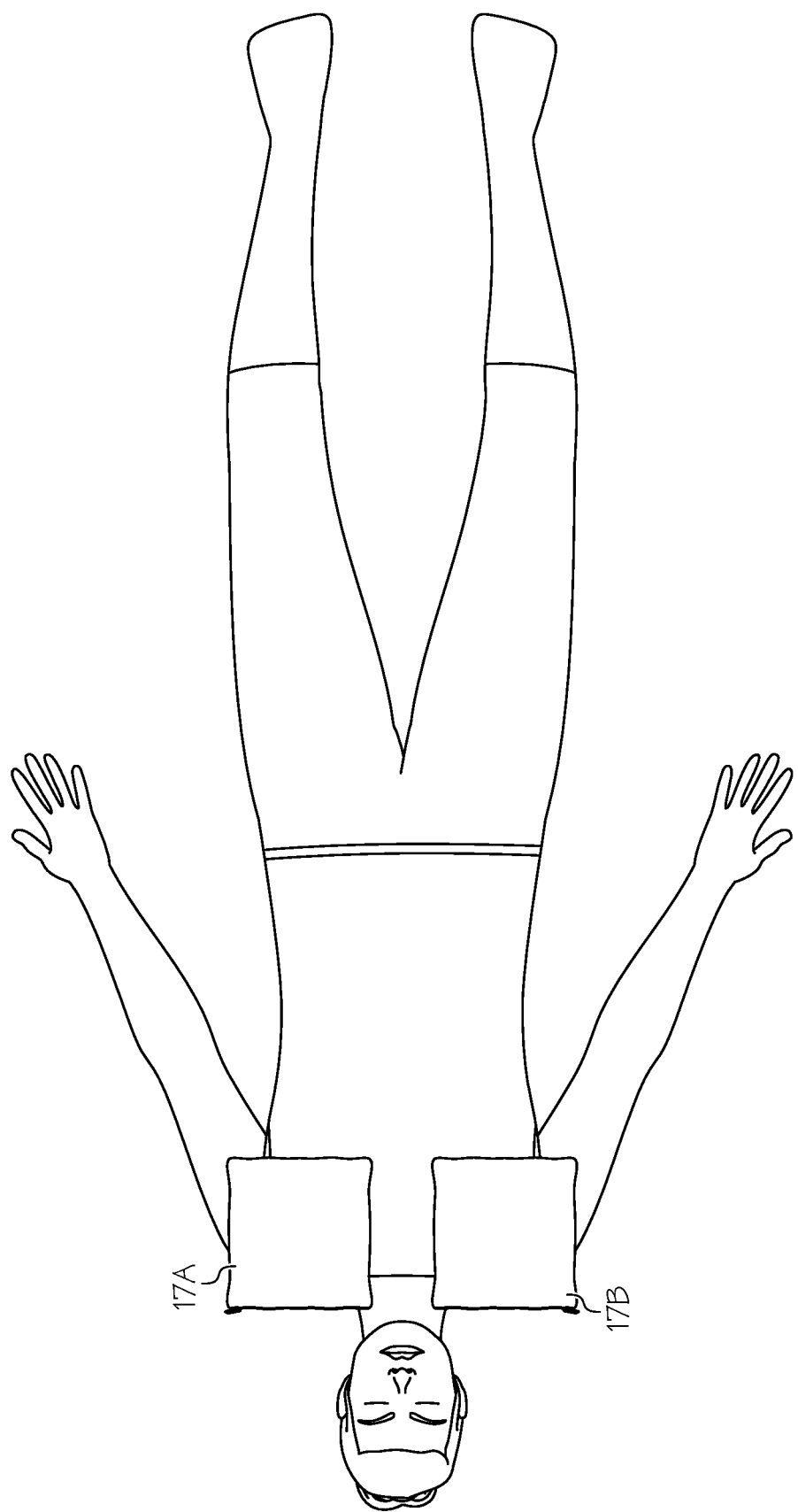
FIG. 9 depicts a perspective view of an exercise practitioner using the exercise device of FIG. 1 in an exemplary restorative pose.

FIG. 9 shows the practitioner in a restorative relaxation pose. In this relaxation pose, the practitioner may selectively desire to apply heat to a body part or apply cold to a body part. Similarly, after an exercise activity the practitioner may selectively desire to apply heat to a body part or apply cold to a body part. In some versions of exercise device (1), plurality of granules (40) are microwavable. In some versions of exercise device (1), plurality of granules (40) are freezable. In some versions of exercise device (1), plurality of granules (40) are both microwavable and freezable.

With respect to heating a body part, the practitioner moves zipper assembly (9) into the open orientation and removes insert (17) from pouch (15). The practitioner thereafter places insert (17) into a microwave or similar heating device and heats insert (17), and more particularly, heats plurality of granules (40). Thereafter, the practitioner applies the heated insert (17) to the desired body part, as shown in FIG. 9 with insert (17A).

Conversely, with respect to cooling a body part, the practitioner moves zipper assembly (9) into the open orientation and removes insert (17) from pouch (15). The practitioner thereafter places insert (17) into a freezer or similar cooling device and cools insert (17), and more particularly, cools plurality of granules (40). Thereafter, the practitioner applies the cooled insert (17) to the desired body part, as shown in FIG. 9 with insert (17B).

While insert (17) is described as providing heating or cooling in a restorative pose, the entire exercise device (1) may be used as well, if desired by the practitioner. Similarly, heating or cooling may be omitted and exercise device (1) or insert (17) may simply be applied to a body part to provide pressure and weight to a body part of the practitioner. Further, the practitioner may use insert (17) or exercise device (1) as a pillow to rest the practitioner's head or other body parts. Thus, in addition to those features described above with respect to the gripping and sliding of exercise device (1), insert (17) may be used as either a heating pad/pack, a cooling pad/pack, or simply provide weight for the practitioner in furtherance of recovery from an exercise activity, a relaxation activity, or both.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An exercise device comprising: (a) a pouch, wherein the pouch comprises: (i) a first element, wherein the first element comprises a first outer layer and a first inner layer, (ii) a second element, wherein the second element comprises a second outer layer and a second inner layer, wherein the first outer layer and the second outer layer are different, and (iii) a pocket, wherein the pocket is defined by the pouch between the first element and the second element; and (b) an insert, wherein the insert comprises: (i) an outer layer, (ii) an internal cavity defined by the outer layer, and (iii) a plurality of granules disposed in the internal cavity, wherein the insert is sized to be selectively disposed within the pocket.

Example 2

The exercise device and methods of any of the previous or subsequent Examples, wherein the first outer layer comprises a gripping fabric.

Example 3

The exercise device and methods of any of the previous or subsequent Examples, wherein a layer of bamboo batting material is disposed between the first outer layer and the first inner layer.

Example 4

The exercise device and methods of any of the previous or subsequent Examples, further comprising a plurality of gripping nodules, wherein the plurality of gripping nodules are disposed on the first outer layer.

Example 5

The exercise device and methods of any of the previous or subsequent Examples, wherein the second outer layer comprises a synthetic fabric.

Example 6

The exercise device and methods of any of the previous or subsequent Examples, wherein a layer of bamboo batting material is disposed between the second outer layer and the second inner layer.

Example 7

The exercise device and methods of any of the previous or subsequent Examples, further comprising an antimicrobial coating, wherein the antimicrobial coating is disposed on the second outer layer.

Example 8

The exercise device and methods of any of the previous or subsequent Examples, wherein the first outer layer comprises a gripping fabric, wherein the second outer layer comprises a synthetic fabric.

Example 9

The exercise device and methods of any of the previous or subsequent Examples, wherein the first outer layer is associated with a first frictional coefficient when moved along a surface, wherein the second outer layer is associated with a second frictional coefficient when moved along the surface, wherein the first frictional coefficient is greater than the second frictional coefficient.

Example 10

The exercise device and methods of any of the previous or subsequent Examples, further comprising: (a) a first fabric, wherein the first outer layer comprises the first fabric; (b) a second fabric, wherein the second outer layer comprises the second fabric; and (c) a third fabric, wherein the first inner layer comprises the third fabric, wherein the second inner layer comprises the third fabric.

Example 11

The exercise device and methods of any of the previous or subsequent Examples, further comprising: (a) a first layer of antimicrobial batting material, wherein the first layer of antimicrobial batting material is disposed between the first outer layer and the first inner layer; and (b) a second layer of antimicrobial batting material, wherein the second layer of antimicrobial batting material is disposed between the second outer layer and the second inner layer.

Example 12

An exercise device comprising: (a) a pouch, wherein the pouch comprises: (i) a gripping element, wherein the gripping element comprises a gripping fabric layer, a first batting fabric layer, and a first internal fabric layer, wherein the first batting fabric layer is disposed intermediate the gripping fabric layer and the first internal fabric layer, (ii) a sliding element, wherein the sliding element comprises a synthetic fabric layer, a second batting fabric layer, and a second internal fabric layer, wherein the second batting fabric layer is disposed intermediate the synthetic fabric layer and the second internal fabric layer, (iii) a pocket, wherein the pocket is defined by the gripping element and the sliding element, and (iv) a zipper assembly, wherein the zipper assembly is configured to selectively provide access to the pocket and prevent access to the pocket; and (b) an insert, wherein the insert comprises: (i) an outer layer, (ii) an internal cavity defined by the outer layer, and (iii) a plurality of microwavable granules disposed in the internal cavity, wherein the insert is sized to be selectively disposed within the pocket.

Example 13

The exercise device and methods of any of the previous or subsequent Examples, wherein the first batting layer and the second batting layer comprise an antimicrobial bamboo batting material.

Example 14

The exercise device and methods of any of the previous or subsequent Examples, wherein the fabric layer comprises a plurality of gripping features.

Example 15

A method of exercising comprising: (a) disposing an inset filled with a plurality of granules into a pocket of a pouch to form an exercise device; (b) positioning the exercise device in a first orientation relative to a surface, wherein a first outer surface of the pouch abuts the surface in the first orientation; (c) exerting a sliding force on the exercise device against the surface, wherein the first outer surface prevents the pouch from sliding on the surface in response to the sliding force; (d) positioning the exercise device in a second orientation relative to the surface, wherein a second outer surface of the pouch abuts the surface in the second orientation; (e) exerting the sliding force on the exercise device against the surface, wherein the second outer surface allows the pouch to slide on the surface in response to the sliding force; and (f) removing the insert from the pocket of the pouch.

Example 16

The exercise device and methods of any of the previous or subsequent Examples, further comprising: (a) after removing the insert from the pocket of the pouch, heating the insert; and (b) heating a body part by placing the insert on the body part.

Example 17

The exercise device and methods of any of the previous or subsequent Examples, wherein the plurality of granules are microwavable granules.

Example 18

The exercise device and methods of any of the previous or subsequent Examples, further comprising: (a) after removing the insert from the pocket of the pouch, cooling the insert; and (b) cooling a body part by placing the insert on the body part.

Example 19

The exercise device and methods of any of the previous or subsequent Examples, wherein the plurality of granules are freezable granules.

Example 20

The exercise device and methods of any of the previous Examples, wherein the pouch includes a layer of bamboo batting, wherein the second outer surface is antimicrobial.

V. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An exercise device comprising:
    (a) a pouch, wherein the pouch comprises:
        (i) a first element, wherein the first element comprises a first outer layer and a first inner layer,
        (ii) a second element, wherein the second element comprises a second outer layer and a second inner layer, wherein the first outer layer and the second outer layer are different,
        (iii) a pocket, wherein the pocket is defined by the pouch between the first element and the second element,
        (iv) a first fabric, wherein the first outer layer comprises the first fabric,
        (v) a second fabric, wherein the second outer layer comprises the second fabric,
        (vi) a third fabric, wherein the first inner layer comprises the third fabric, wherein the second inner layer comprises the third fabric,
        (vii) a first layer of antimicrobial batting material, wherein the first layer of antimicrobial batting material is disposed between the first outer layer and the first inner layer, and
        (viii) a second layer of antimicrobial batting material, wherein the second layer of antimicrobial batting material is disposed between the second outer layer and the second inner layer; and
    (b) an insert, wherein the insert comprises:
        (i) an outer layer,
        (ii) an internal cavity defined by the outer layer, and
        (iii) a plurality of granules disposed in the internal cavity,
        wherein the insert is sized to be selectively disposed within the pocket.

2. The exercise device of claim 1, wherein the first outer layer comprises a gripping fabric.

3. The exercise device of claim 2, wherein a layer of bamboo batting material is disposed between the first outer layer and the first inner layer.

4. The exercise device of claim 2, further comprising a plurality of gripping nodules, wherein the plurality of gripping nodules are disposed on the first outer layer.

5. The exercise device of claim 1, wherein the second outer layer comprises a synthetic fabric.

6. The exercise device of claim 5, wherein a layer of bamboo batting material is disposed between the second outer layer and the second inner layer.

7. The exercise device of claim 5, further comprising an antimicrobial coating, wherein the antimicrobial coating is disposed on the second outer layer.

8. The exercise device of claim 1, wherein the first outer layer comprises a gripping fabric, wherein the second outer layer comprises a synthetic fabric.

9. The exercise device of claim 1, wherein the first outer layer is associated with a first frictional coefficient when moved along a surface, wherein the second outer layer is associated with a second frictional coefficient when moved along the surface, wherein the first frictional coefficient is greater than the second frictional coefficient.

10. An exercise device comprising:
    (a) a pouch, wherein the pouch comprises:
        (i) a gripping element, wherein the gripping element comprises a gripping fabric layer, a first batting fabric layer, and a first internal fabric layer, wherein the first batting fabric layer is disposed intermediate the gripping fabric layer and the first internal fabric layer,
        (ii) a sliding element, wherein the sliding element comprises a synthetic fabric layer, a second batting fabric layer, and a second internal fabric layer, wherein the second batting fabric layer is disposed intermediate the synthetic fabric layer and the second internal fabric layer,
        (iii) a pocket, wherein the pocket is defined by the gripping element and the sliding element, and
        (iv) a zipper assembly, wherein the zipper assembly is configured to selectively provide access to the pocket and prevent access to the pocket; and
    (b) an insert, wherein the insert comprises:
        (i) an outer layer,
        (ii) an internal cavity defined by the outer layer, and
        (iii) a plurality of microwavable granules disposed in the internal cavity,
        wherein the insert is sized to be selectively disposed within the pocket.

11. The exercise device of claim 10, wherein the first batting layer and the second batting layer comprise an antimicrobial bamboo batting material.

12. The exercise device of claim 11, wherein the fabric layer comprises a plurality of gripping features.

* * * * *